United States Patent
Xie et al.

(10) Patent No.: US 10,335,172 B2
(45) Date of Patent: Jul. 2, 2019

(54) METHODS AND APPARATUS FOR PREPARING A HEMISPHERICAL SURFACE

(71) Applicants: Ping Xie, Ashland, MA (US); Xue Li, Ashland, MA (US)

(72) Inventors: Ping Xie, Ashland, MA (US); Xue Li, Ashland, MA (US)

( * ) Notice: Subject to any disclaimer, the term of this patent is extended or adjusted under 35 U.S.C. 154(b) by 877 days.

(21) Appl. No.: 13/844,955

(22) Filed: Mar. 16, 2013

(65) Prior Publication Data

US 2014/0271005 A1    Sep. 18, 2014

(51) Int. Cl.
*A61B 17/16* (2006.01)
*A61B 17/17* (2006.01)

(52) U.S. Cl.
CPC ...... *A61B 17/1746* (2013.01); *A61B 17/1617* (2013.01); *Y10T 408/03* (2015.01)

(58) Field of Classification Search
CPC . A61B 17/16; A61B 17/1664; A61B 17/1666; A61B 17/1746; B23D 77/04; B23D 2277/08; B23D 2277/081; B23D 2277/80
See application file for complete search history.

(56) References Cited

U.S. PATENT DOCUMENTS

| | | | | |
|---|---|---|---|---|
| 5,755,719 A * | 5/1998 | Frieze | ............... | A61B 17/1666 606/81 |
| 6,979,335 B2 * | 12/2005 | Lechot | ............... | A61B 17/1666 606/80 |
| 7,097,646 B2 * | 8/2006 | Schantz | ............. | A61B 17/1666 606/81 |
| 7,479,144 B2 * | 1/2009 | Myers | ............... | A61B 17/1617 606/80 |
| 7,722,615 B2 * | 5/2010 | Botimer | ............ | A61B 17/1666 606/80 |
| 8,771,275 B2 * | 7/2014 | Xie | .................... | A61B 17/1666 606/81 |
| 9,011,442 B2 * | 4/2015 | Victor | ............... | A61B 17/1666 606/80 |
| 2010/0076442 A1 | 3/2010 | Xie et al. | | |

* cited by examiner

*Primary Examiner* — Anu Ramana
(74) *Attorney, Agent, or Firm* — Da Vinci Partners LLC; John Moetteli

(57) ABSTRACT

Methods and apparatus for preparing at least a hemispherical surface with a desired dimension have been disclosed. The method includes at least two steps: a primary cutting mode for mostly reaming a lower portion of the target site, which enveloped area from the pole to intermediate latitude and a finishing cutting mode for reaming either an upper portion or an entire area of the site by less number of times of rotation, respectively. The intermediate latitude locates between the pole and the equator of hemisphere.

12 Claims, 9 Drawing Sheets

Primary mode 16

Finishing mode 18

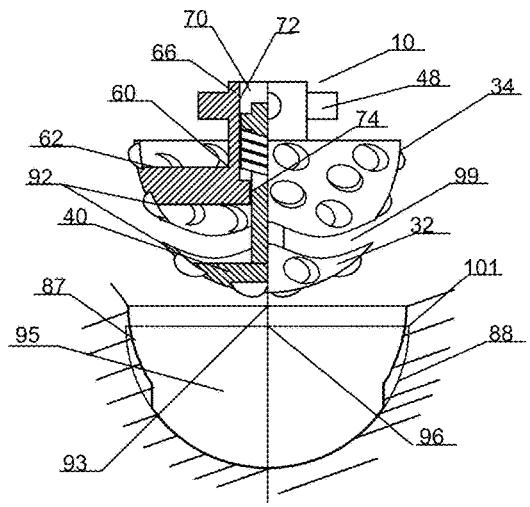
Primary mode 16
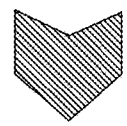
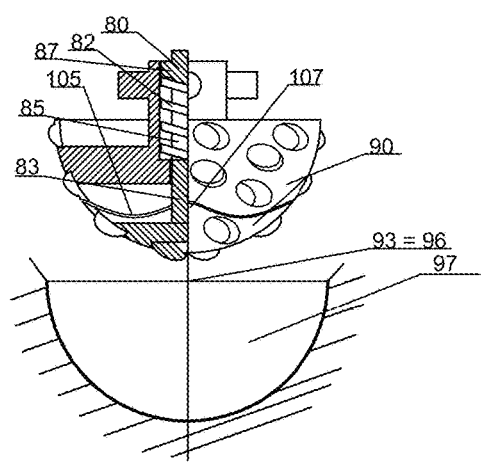
Finishing mode 18
Figure 2

- Providing an adjustable reamer attaching to the driving shaft.

- Inserting the reamer into a target site, while it is in the second position.

- Positioning the reamer from second position to first position.

- Reaming the site, while the reamer is in first position, until reaching a desired floor condition and depth.

- Adjusting the reamer from first position to second position, while the reamer is reaming.

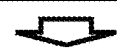

- Reaming the site until forming a full continuous hemispherical surface.

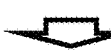

- Removing the reamer out of the site, while the reamer is in first position.

A first enbodiment of the method.

Figure 4.

- Providing an adjustable reamer attaching to the driving shaft.

- Inserting the reamer into a target site, while it is in the first position.

- Reaming the site, while the reamer is in first position, until reaching a partial hemispherical surface having a desired floor condition and depth.

- Adjusting the reamer from first position to second position, while the reamer is reaming.

- Reaming the site until forming a full continuous hemispherical surface.

- Removing the reamer out from the site, while the reamer is in second position.

A second enbodiment of the method.

Figure 6.

- Providing a primary reamer attaching to the driving shaft and inserting the reamer into a target site.

- Reaming the site until reaching partial hemisphere having a desired floor condition and depth.

- Removing the primary reamer out of the site and interchange to a finishing reamer.

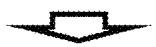

- Inserting the finishing reamer to the site

- Reaming the site, until forming a full continuous hemispherical surface.

- Removing the reamer out from the site.

A third enbodiment of the method.

METHODS AND APPARATUS FOR PREPARING A HEMISPHERICAL SURFACE

FIELD OF INVENTION

The present invention relates to methods and apparatus for preparing a hemispherical surface with a desired dimension in separated, partially cutting steps. In particular, the invention relates to the procedure of preparing the acetabulum cavity for surgery of the hip replacement and other fields beyond medical.

DESCRIPTION OF THE PRIOR ART

A process of cutting a full or partial hemispherical surface by a single dimension rotation tool (like a lathe) always meets a problem of zero or a lower cutting speed at pole area or nearby the sphere. In the medical field, a process of reaming the defected acetabulum in surgery of the hip replacement has been met with the same problem and should always be considered as a critical challenge to the overall outcome of implanting the prosthesis from many aspects of concern. If directly using the identical size of the dome-like reamer reams the cavity, the difference in the cutting rate between the pole and equator point will cause significant excess cutting in the equator area, but not in the polar area.

From practical experiences, the smaller reamer used is easier to ream the apex area of the cavity, due to the small difference of cutting rate from the point of the apex to the equator. In order to reduce the uneven cutting problem, acetabular reamers used in the prior art, generally include using a series of reusable, hemispherical dome-like reamers, with a progressive increment of diameter. The difference in diameter between adjacent reamers is about 2 mm. The procedure of reaming the defected acetabulum always starts with a smaller sized reamer, such that the size is similar to or smaller than the existing cavity, or at least two sizes smaller than the size of preoperatively selected acetabular prosthesis. The smaller reamer used is more convenient for reaming the area near the pole by swinging the shaft handle away from the longitude axis of the sphere, with less damage on the upper portion of the hemisphere. Then the surgeon can create step by step interchanges for the next reamer, using a larger size reamer to enlarge the diameter of the cavity, until reaching the desired size. Reaming hemisphere by progressive reamers somehow is repetitive, but not the ideal choice, particularly for the robot system.

In general, reaming the defected hemispherical acetabulum normally needs step by step interchanging at least 3-5 serials reamers. It is conceivable that each operation step must be carefully carried out, in terms of repeatedly positioning reamer in same direction of the spherical axis and controlling a proper depth cut by each reamer, as well as avoiding tissue damages during inserting and removing of the reamer from incision site. In the case of manually operating the reamer, in which there is a small incision and a limited view, it is a challenge for surgeon's experience and skill. Otherwise, missing the direction of the axis of the hemisphere and improperly controlling a depth cut of the cavity to correspond to the size of each reamer used will cause variation of the dimension, surface, and orientation of the cavity cut. Obviously, it is unavoidable during reaming with repeatedly interchanging reamers, that surgeons require aid from CAOS. From the point of view of the clinic, a solution for overcoming these problems through either the improved method, the better apparatus used in reaming acetabulum, or both, are strongly desired.

Furthermore, the navigation and robotic technologies (CAOS) have become more and more popular in hip replacement surgery due to their potential in filling unmet needs in respect to the total surgical quality and long term results of operation. However, because of outdated procedures currently associated with robotic systems, particularly, frequently interchanging reamer heads during reaming, surgeons, until now, have not seen that robots perform as well as or better than humans, in terms of skill and flexibility. It becomes a major hurdle in promoting the robot system for hip replacement surgery. So in order to explore the overall functions and advantages of the robot in surgery, the market needs is far beyond how good the robot is, but how well the state of the art of surgical technologies can associate with the robot system interms of tooling, prosthesis design and procedures of the hip replacement. In particular, a desirable method is where there are few steps or a nonchanging reamer head during reaming and a better accuracy of the spherical surface.

SUMMARY OF THE INVENTION

The present invention here dedicates suitable apparatus and cutting methods for respectively reaming section of the hemispherical surface in various steps. In general, it includes successive steps of: a primary cutting mode for reaming the lower (first) portion of the target site, typically dedicated as Zone A of a hemisphere, in FIG. 1 and a finishing (or secondary) cutting mode either for reaming upper (or second) portion of the target site, typically dedicated as Zone B of a hemisphere, in FIG. 1, or for reaming the entire area of the hemisphere.

The first advantage is, the method could possibly generate a hemisphere by using only two reamers or by a single reamer, which can precisely execute both cutting modes, without frequently interchanging the reamer head as done in conventional procedures in hip replacement surgery and scarifying the quality of the cavity reamed.

The second advantage is, the apparatus's method is suitable for various designs in order to be applicable for various stages or types of operation, such as MIS, resurfacing and revision of the hip replacement surgery.

The third advantage is, that any available principle/techniques for cutting hemisphere, such as types of cutting element used, are suitable to be adopted by the reamer design in the present invention, such as the conventional thin-wall hemispherical dome reamer and others disclosed in the prior art.

The fourth advantage is that the design of the reamer includes a limited number of parts, so it can consistently and reliably move between the first and second positions. Further, the reamer can be made in a less expensive and disposable format.

A fifth advantage is that once the method for cutting hemisphere is applied in the clinical setting, it will save on operation time, correct human errors, and provide an accurate and qualitative acetabular cavity in many respects.

An other advantage is, the acetabular reamer in the present invention can appeal to a wide range of orthopedic surgeons with various skills and experiences. Further yet, the training and skill level required to use the method and reamer, as well as to become proficient with it, is not overly taxing on the orthopedic surgeon.

Further yet, the cutting method and apparatus for reaming a hemispherical surface are fully compatible with manual and various navigation and robotic systems used in hip replacement surgery, which are able to explore overall capabilities and advantages of performance and results of the surgical robot exceeding human ability.

BRIEF DESCRIPTION OF THE DRAWINGS

The above-mentioned features and advantages of this invention, and the manner of attaining them, will become more apparent and understood by reference to the following description of embodiments of the invention taken in conjunction with the accompanying drawings, wherein:

FIG. 2. A first preferred structure of an adjustable reamer has a lower and an upper cutting surface configured by a cutting element of a thin-wall dome, which are arranged and switchable along the longitude axis of the hemisphere.

FIG. 4. A flow chart of a reaming method (steps) corresponds to the first and second performed embodiment of apparatus.

FIG. 6. A flow chart of a reaming method corresponds to the third and fourth preferred embodiment of apparatus.

FIG. 7. A flow chart of a reaming method corresponds to the fifth preferred embodiment of apparatus.

SPECIFIC DESCRIPTION OF THE PREFERRED EMBODIMENT

The apparatus, method, and steps of the present invention are now described in more detail. Some of these details described in the method and apparatus are known to those skilled in the art and will not be discussed in great detail. Further, experienced individuals will appreciate that certain steps may be altered or omitted while other steps may be added without departing from the scope of the invention. The novel method and apparatus of the present invention, for example, can be applied to surgery of hip arthroplasty, to revision surgeries for total and partial hip replacement, as well as to other fields beyond the orthopedic surgeries and the medical field.

Figure 1:
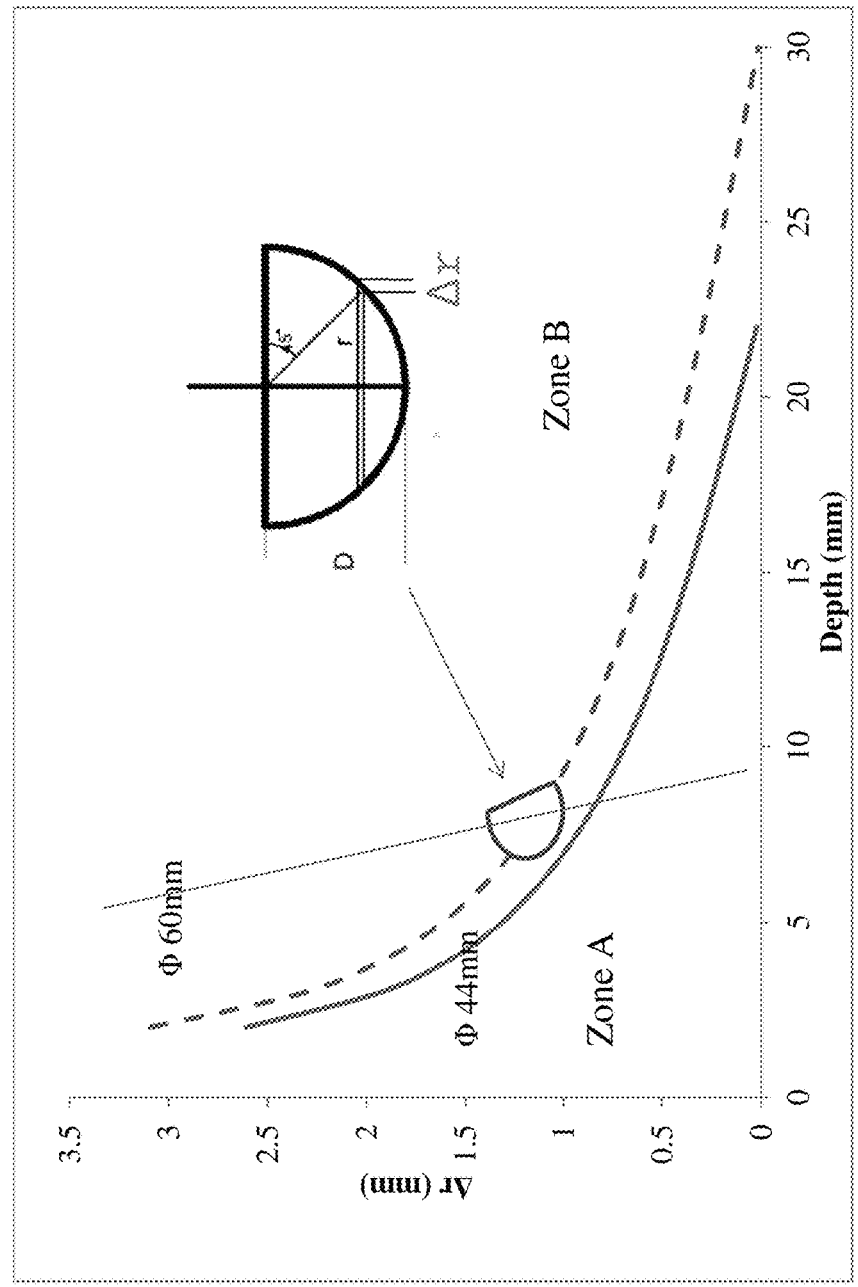
FIG. 1. The radial radius variation (Δr) between adjacent layers v.s. a depth of the hemisphere. Two cutting zones divided by radius variation.

The Principle of the Method:

Any hemisphere with a desired dimension can be imagined as one stacked up a plurality of circular rings with a progressive increased radius ($r_i$) along the polar axis of the hemisphere. FIG. 1 has shown: X axis is a depth (D) or radius (K) of the hemisphere and Y axis is the difference of the horizontal radius between adjacent rings, marked as $\Delta r_i = r_i - r_{i-1}$, defining as the horizontal distance from a point on the hemispherical surface to the axis of the hemisphere. The location of each ring (i) corresponds a specific depth or height hemisphere. The increment of interval of depth is about 1 mm along the polar axis of the hemisphere. The dot line curve here represents data from a hemisphere with a radius (R) of 30 mm and solid line curve represents one with the radius of 22 mm.

The curve in FIG. 1 has explored a typical uneven change rate, $\Delta r_i$ corresponding to each circle radius of the ring (i). For one dimension cutting mode, a linear cutting speed (called a cutting speed) applied at each point of hemispherical surface is solely proportional to the horizontal radius ($r_i$) of each layer (the ring). So at the pole point, the radius and the cutting speed all are zero. At the equator, the radius and the cutting speed reach maximum level, regardless of the radius of the sphere. The principle used in the CNC machine is different speed applied on the corresponding point of sphere would bring a uniform cutting effect at each point. In other words, the final linear cutting effect at each point of the sphere can be compensated by continuously varying turning speed. Of course, the more speed zone applied, the better or more uniform cutting effect is. In reality, the curve in FIG. 1 could be divided into at least two zones: 1) a zone A having a sharply increasing speed of cutting with the depth, which represents area from the pole to intermediate latitude in left side of FIGS. 1 and 2) a zone B having a slow/flat increasing speed of cutting with the depth, which represents area from the intermediate latitude to the equator in the right side of FIG. 1. A position of the intermediate varies little with the radius of the sphere.

In the zone A, the linear cutting rate is rapidly decreasing while the depth approaches near zero. In contrary, zone B, changes a little while the depth approaches to equator. Such that the phenomena leads to two conclusions: 1) there is no way to ream a perfect hemisphere by one dimensional rotation of cutting, solo, or even cutting speed, because significant differences of the cutting speed will be distributed throughout the overall cutting area. 2) Various cutting frequencies or number of times of rotation applied at different radius zones would somehow compensate for uneven cutting.

In other words, the effects of the circle radius difference, $\Delta r_i$ could be compensated by either a specific total number of cutting times or cutting frequency applying on each point or latitude. For example, the cutting effect of a higher cutting frequency applied at area with smaller circle radius, $r_i$, (near the pole) could perform similarly or closely to one of a lower cutting frequency applied at the ara (near equator) with larger circle radius. By the same token, any method or apparatus which can reduce or postpone the cutting efficiency acted on an ara with a larger circle radius, $r_i$ (in a upper cutting layer) of the hemisphere also behaves similar to the effect of the cutting frequency compensation (CFC), when the reamer is rotated by even cutting speed. But in reality, multiple cutting speeds applied might be too complicated to design a device. To particularly extend such the idea of CFC, one could define it into at least two cutting speed zones or equivalent, such as a primary cutting mode for cutting lower portion of the target site (the bottom area near pole of the hemisphere (zone A)) and a finishing mode either for reaming upper portion of the target site, typically dedicated as Zone B of a hemisphere, in FIG. 1, or for reaming the entire area of the hemisphere (including zone A and zone B together) after accomplishing the primary mode. The method or procedure could be applied in either simultaneous or successive cutting modes on each zone area by either different cutting frequencies or different number of cutting times. A typical successive example is first partially reaming or not reaming the upper portion, while fully reaming the lower portion of the site in the primary mode, then reaming both zones together until reaching a full continuous hemispherical surface.

According to the principle described above, any type of the cutting element equipped in the reamer disclosed in the prior art should be used and be suitable for designing apparatus and implementing the method, if the cutting element used can present a dynamic spherical cutting profile in a partial or full hemispherical form, while it is rotated around the longitude axis. For instance, such as a thin shell dome-like reamer with a cutting teeth in conventional reamer, a semi-circular blade as disclosed in U.S. Pat. No. 5,755,719 by Frieze, in which the semi-circular blade has the same radius of the curvature as the spherical one of the cutting target and rotates around the polar axis of the hemisphere, or a circular blade(s) as a cutting element is positioned in a manner of that its turning axis diverges from the longitudinal axis of the hemisphere by a certain angle as disclosed in publication of US 20100076442 by Xie, all could be used.

The typical zone A here represents the area from the pole to the intermediate latitude. The intermediate latitude is located between the pole and the equator of the hemisphere. The zone B represents the area from the intermediate latitude to the equator of the hemisphere. The boundary line (or intermediate latitude) between two zones is approximately located at a range of 35-55 degree latitude of hemisphere (here the pole=90 degree latitude) and varied with the radius of the sphere to be cut. The more preferred intermediate latitude is at 45 degree latitude.

The present invention hem dedicates a cutting method for preparing a full continuous hemispherical surface, which includes both concave and convex surface.

Particularly, the method primarily dedicates successive steps including: respectively reaming bottom (first) and upper (second) portions of the hemispherical surface in separated steps. For instance, a primary cutting mode for mostly reaming the lower latitude area or the bottom portion of the hemisphere, typically dedicated as Zone A in FIG. 1, in order to generate a partial hemisphere with a desired dimension and a finishing (secondary) cutting mode either for reaming the upper portion of the target site, typically dedicated as Zone B of a hemisphere, in FIG. 1, or for reaming the entire area (Zone A and Zone B together) of the hemisphere after accomplishing the primary mode. Of course; an apparatus having more than two layers of cutting surface could also be an option for completing the process above.

As discussed, the method is directly related to a method of separately, or step by step cutting of each specific area of the hemisphere, which is quite different from serially cutting the same area by frequently interchanging the reamer head with a increasing size in the conventional procedure. A single, or at most, two reamers having identical spherical cutting radius can complete reaming the cavity with a desired size, quality and a shape, which significantly simplifies the procedure of reaming and avoids many unnecessary steps and mistakes as realized.

In the primary mode, as one option, the surgeon firstly rotates the reamer with the lower cutting surface (covering Zone A) for fully reaming a bottom portion of the target site. The lower cutting surface could be either a primary reamer having a fixed, partial dynamic hemispherical cutting surface or an adjustable reamer in the first position with a first shape. The adjustable reamer comprises at least a lower and upper cutting surface, but in the primary cutting mode, the upper one is not in working position or is not fully functioning. The lower cutting surface in both reamers has a desired spherical radius and has dynamically enveloped the area from pole to intermediate latitude of the hemisphere (presented the zone A), in order to at least form the partial hemisphere in the bottom portion. In this mode, the surgeon could implement enough rotations on the area near the pole without concern for overcutting the other sections above.

In the finishing mode, t surgeon uses either the adjustable reamer having a second shape while it is in second position (both cutting surfaces are in working position) or a finishing reamer with a fixed, full continuous dynamic hemispherical cutting surface, like a regular dome-like acetabular reamer to ream the entire area of the site. Both cutting surfaces in the reamer have a desired spherical radius and are the same as one of the lower cutting surface. This step takes less time and effort on enlarging the upper section of the hemisphere as well smoothing the entire surface because of the higher efficiency of the full size reamer used as discussed. In other words, the total number of cutting times applied in the primary mode is at least 2 folds more than the one in the finishing mode. In general, during the primary mode, CFC might be implemented in a manner of groups selected from a) non-cutting upper section, b) partial-cutting upper section of the hemisphere. As an alternative of CFC, one could also simultaneously cut the upper section of the site by lowering the frequency of rotation, while the lower section of hemisphere is cut by a higher frequency rotation of cutting, respectively.

The following detailed description is directed to certain specific embodiments of apparatus and method in the present invention. However, the invention can be embodied in a multitude of different ways or designs as defined and covered by the claims. In this description, reference is made to the drawings herein like parts are designated with like numerals throughout. Furthermore, embodiments of the invention may include several novel features, no single one of which is solely responsible for its desirable attributes or which is essential to practicing the inventions herein described.

According the principle discussed above: in the primary cutting mode, one needs to avoid or reduce reaming the upper section (zone B) of the hemisphere, while fully reaming the bottom portion, which is a major concern of the apparatus design. Reaming the entire section of the hemisphere is the purpose of the finishing cutting mode.

The description now turns to the figures. The illustrated example embodiments will be best understood by reference to the figures. The following description is intended only by way of example and simply illustrates certain example embodiments representative of the invention, as claimed.

According to the procedure discussed above, the first preferred embodiment of apparatus dedicates that a structure of the adjustable reamer having a desired spherical cutting radius comprises of at least two cutting surfaces, a lower and an upper cutting surface. They are arranged in a sequence array and switchable along the longitudinal axis and have a same spherical cutting radius. Either cutting surfaces could be adjustable in movement toward or away from its fixed counterpart. As FIG. 2 shows, the lower cutting surface is a moveable part and has dynamically enveloped an area defined from pole to intermediate latitude of the hemisphere, while the reamer is rotated. The upper cutting surface has been fixed with a frame, which interfaces with the driving shaft. The reamer has two reaming positions: the first position having a first shape wherein the upper surface is partially "hidden" (or partially functioning), and the second position having a second shape: wherein both cutting surfaces of the reamer are in the working position with the same spherical center and form a hemispherical cutting surface (a second shape).

A First Preferred Embodiment of Apparatus

FIG. 2 has shown a typical case of adjustable reamer. The reamer 10 is, in general, configured by a typically cutting element, a truncated, thin shell in a partial hemispherical form. The cutting element is like one in a conventional dome reamer. The lower and upper cutting surfaces are separable or exchangeable along the longitudinal axis and arranged in a sequence array. The lower cutting surface 32 is statically in a partial spherical shape and has enveloped a first area from pole to intermediate latitude of the hemisphere (zone A). The upper cutting surface 34 is in a partial spherical shape and has enveloped the area from the intermediate latitude to the equator of the hemisphere (zone B). Each cutting surface 32 and 34 has same spherical cutting radius, which corresponds to the desired radius of the hemisphere to be cut. Any design, in which one of the cutting surfaces could be moveable toward and away from its fixed counterpart, is also acceptable. When their spherical cutting centers are merged together on same point at the longitudinal axis, it forms a full continuous hemispherical cutting surface 90. Each cutting surface here includes a plurality of cutting teeth regularly distributed on its external hollow surface of the shell. Here the detailed features of such a hollow surface is not discussed in the present invention, because it is well known as one of the conventional dome reamer disclosed in the prior art.

In particular, the adjustable reamer 10 further comprises following parts: a first base 40, which is integrally attached to internal surface of the hollow, lower cutting surface 32. A second base 60 is a T-shape frame and has one vertically upward branch and two horizontal ends 62, which have integrally fused with internal surface of the hollow upper cutting surface 34. Its vertical branch is a cylinder arm 66, which comprises an interface located at its proximal end. The interface typically comprises two, three, or four outward radial posts 48, respectively, in order to engage with a female interface at distal end of the driving shaft (not shown). There is a stepped, through-hole 70 at a center of the cylinder arm 66 along its longitudinal axis, which includes: a square hole 74 at its lower portion of the hole 70 and a round hole 72 at supper portion of the hole 70.

A connection rod 80 comprises three types of cross sections distributed along its longitudinal axis: a square profile section 83 in a distal portion of rod 80 has a dimension for sliceable fitting into the square hole 74 of the through-hole 70, a first rod section 85 at the middle of rod 80 has a diameter of at least 2 mm smaller than one of the round hole 72 and a second rod section 87 at the upper portion of rod 80 has a diameter for sliceable fitting into the round hole 72 of the through-hole 70. So the rod 80 is sliceable within the stepped hole 70, when assembled.

A press spring 82 has an inside diameter comparable with the first rod section 85 of the connection rod 80 and an outside diameter fit into the round hole 72 of the through-hole 70. The connection rod 80 is a connecting linkage for assembling both the lower and the upper cutting surfaces 32, 34 together in one piece. The connection rod 80 with a spring 82 on the position, firstly passes through a center of the hole 70 of the cylinder arm 66, then firmly engages with the first base 40 by its distal end of square section 83 after it passes the square hole 74 of the second base 60 and firmly fixes the lower cutting surface 32 on a position, on which the lower cutting surface 32 is assembled with the upper cutting surface 34 end to end. In that position, the spherical cutting center of the lower cutting surface is equal to the spherical cutting center of the reamer. Since the lower and upper cutting surface merged together, the adjustable reamer forms the full continuous hemispherical cutting surface (seen 90 in FIG. 2). At that position, the spring is in normal (released) condition. This position presents the second shape of the reamer and is referred as an upper end point of the lower cutting surface 32 and is defined as the second (fused) position 90 of the reamer 10. If any kind of external force (from actuating rod of shaft assembly) is applied to the proximal end of the connection rod 80, such as actuating mechanism of driving shaft, the lower cutting surface 32 could shift down and move away from the upper cutting surface 34 until a lowest end point (while the spring is pressed) that presents the first shape of the reamer and is defined as a first (spaced away) position 92 of the reamer 10 (finishing mode in FIG. 2). At the first position, the first spherical virtual center 96 of the lower cutting surface 32 (it is also the spherical cutting center of the reamer) offsets from the second virtual center 93 of the upper cutting surface 34 by an offset distance 99. At this position 92, the cutting track 87 of the upper cutting surface 34 is far above surface 88 while the reamer is in the second position 90. The entire cutting track 95 of the reamer 10 as shown in FIG. 2, brings about a consequent less cutting of the upper portion (at imaginary equator) of the hemisphere.

The offset distance 99 between two virtual centers or points, typically should be at a range from zero to at least 5 mm. At the first position 92, the largest diameter of cross section at an upper portion reamed by the upper cutting surface should be about 2 mm less than the diameter 101 of the imaginary equator (see FIG. 2). So the apparatus accomplishes the primary cutting mode in a manner of partially cutting the upper section of the hemisphere. The offset distance 99 can be continually adjusted by actuating the mechanism affiliated with the driving shaft assembly, when the reamer attaches with the assembly.

When the lower and upper cutting surface is merged in the second position 90 (offset distance is zero), the reamer is in a good shape for processing the finishing mode and is able to form the fill continuous hemispherical cutting track 97. In order to guarantee that the transition area between two portions or reaming zones of the hemispherical surface are fully covered and smoothly reamed without a gap, the lower cutting area (edge) 105 of the upper cutting surface 34 and the higher cutting area (edge) 107 of the lower cutting surface 32 might be partially interlaced or overlapped at their adjacent or transition latitude, comparable to a jig-saw pattern or similar.

An alternative configuration or mechanism for adjusting the position of the lower cutting surface 32 to various positions is suitable too. Instead using the press spring 82 paired with the actuating mechanism on the shaft assembly for holding and releasing the position of the lower cutting surface 32 (by moving the first base 40) with a respect to the upper cutting surface 34, any kind of mechanism affiliated with the second base 60, which is able to lock the position of the lower cutting surface 32 along the longitudinal axis, can also be considered. For instance, to manually adjust the lower cutting surface 32 to the first position 92 and to the second position 90 or multiple positions (not shown), respectively, will allow surgeons to take the reamer out from the site at any point during the primary mode, check status of the cavity, and then press the releasing button manually shifting the position of the reamer and relocking it while the primary mode is completed.

A Second Preferred Embodiment of Apparatus

Instead using the hollow thin-wall (partial) dome as a cutting element forming a cutting surface, according to mechanisms of cutting sphere disclosed in prior art, any other type of the cutting elements are suitable to form either the lower or the upper cutting surface or both, if its dynamic cutting profile is in either partial or full hemispherical form, when the reamer rotates around polar axis of the hemisphere.

For instance, one type of the cutting element disclosed in U.S. Pat. No. 5,755,719 by Frieze and other disclosed in publication of US 20100076442 by Xie could be options for configuring the reamer here. If applied, it brings more advantages to the apparatus and method. Both layers of the cutting surface here can be configured by a same type of those cutting elements mentioned above or a combination from different types.

Figure 3:
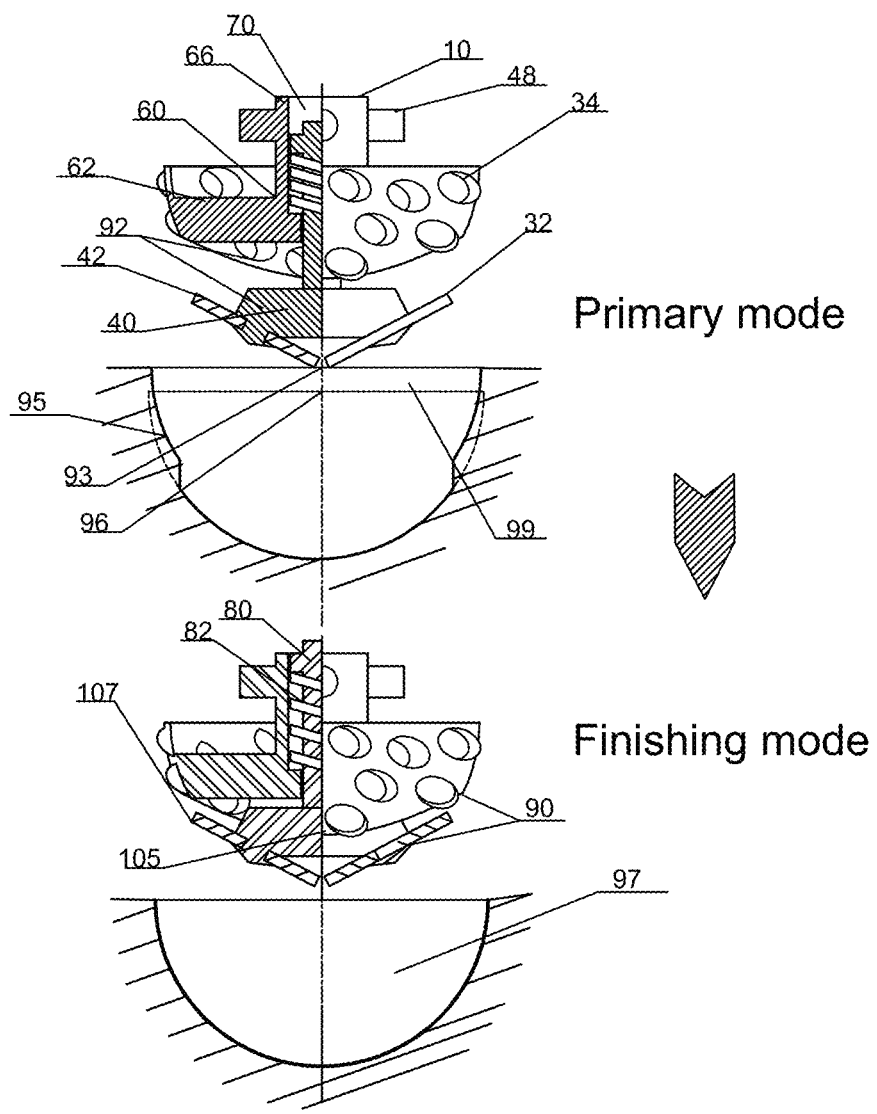
FIG. 3. A second preferred structure of an adjustable reamer has a lower configuration by a cutting element of offset circular blade and an upper cutting surface (a type of thin-wall dome as a cutting element), which are arranged along the longitude axis of the hemisphere and collapsible.

A combination of the cutting element referred to in US 20100076442 has a lower cutting surface and a hollow thin wall partial dome type as the upper cutting surface (shown in FIG. 3). If applied, this takes advantages from both types of the cutting element. The typical characteristic of the zone A has shown that the horizontal radius of the ring varies rapidly from the pole to the intermediate latitude of the sphere, so a linear cutting speed at the upper edge (at intermediate point) of the offset circular blade is much larger than one at its lower edge (at the pole). Such the difference and friction between bone and blade causes the blade self-turning, while the reamer turns. The self-turning or rotating can significantly reduce the cutting efficiency in the area the upper edge of the blade is located and bring additional dimension cutting on the polar area, which significantly overcomes the zero cutting speed problems. The final outcome is compromising the effect from the difference of the horizontal radius and presents more uniform cutting speed on the entire lower portion. Furthermore, the major advantages of upper cutting surface in hollow thin-wall dome form are the characteristic of its self-centralizing, smooth movement and a function of picking up the debris during reaming.

In a second preferred embodiment of the apparatus, there is a major difference from the first embodiment: the reamer 10 has a lower cutting surface, which is configured by two circular blades 42. They have been symmetrically and pivotally mounted on a branched end of the first base 40 in a manner (the dimension of the blades and arrangement positions) as disclosed in US 20100076442. As shown in FIG. 3, two offset blades 42 configure a lower cutting surface 32 and present a partial spherical, dynamic cutting profile, while it rotates around spherical axis. The upper cutting surface 34 for covering Zone B is configured by a partial spherical hollow dome and remains same as one in the first embodiment. The highest point 107 of the lower cutting surface (upper edge of the blade) has overlapped with the lowest point 105 of the upper cutting surface. In the same manner as disclosed in the first embodiment above, the first base 40, connection rod 80 and second base 60 link the lower cutting surface 32 and the upper cutting surface 34 together. Other structures and functions of the reamer remain the same as the one disclosed in the first embodiment.

A First Preferred Embodiment of the Method

As shown in a flow chart of FIG. 4, a method of reaming the hemispherical surface with a desired dimension corresponds to the first and second embodiments of apparatus above. The desired dimension means a spherical radius of the surface as the surgeon intentionally planned, so that the dynamic cutting profile of the reamer used matches the cavity to be cut. The method comprises the steps of:

Step 1, providing an adjustable reamer 10 with a desired size of the cutting profile as disclosed above, which is attached to a driving tool (shaft). The preferred driving tool, such as a shaft assembly driven by motor, affiliates actuating mechanism that is able to continually adjust the position of the reamer 10, when they are coupled together. A preferred design of the shaft assembly (not shown) could include an adjustable tongue-like rod concentrically resided on the inside of tube-like driven shaft. There is an actuating means mounted on the handle of the shaft assembly, which engages with the adjustable rod and can manually push down or release up the connection rod 82 through the adjustable tongue-like rod in order to control the position of the lower cutting surface 32 spaced away from or fused to the upper cutting surface 34.

Step 2, inserting the reamer 10 while it is in the second position 90 (a fused position) having the second shape into a target site, or an incision in surgery, while it has a smaller static profile.

Step 3, adjusting the reamer 10 from the second position 90 to the first position 92 (a spaced apart position) having the first shape, here called a first cutting component. The first shape has at least a dynamic spherical cutting surface at least in the partial hemispherical form for covering zone A. So the lower cutting surface is spaced away from the upper one and will present a larger static profile of the reamer 10. At that position, the reamer is ready for performing the primary cutting mode.

Step 4, reaming a bottom (first) portion of the site by rotating the adjustable reamer in the first position 92 with the first shape, until reaching a desired dimension and floor condition, which includes a proper surface quality (size, shape and smoothness) and depth of the site (see cutting track 95 shown in FIG. 2). This reaming step might take numerous times of rotation. The depth usually is approximately equal to the spherical radius to be cut. The surgeon can stop reaming in any stage in order to check the status of the bone condition and avoid overcutting and then re-insert the reamer. When the primary cutting mode is done, the profile of cross section of the cavity shows a typical cutting track 95 in FIGS. 2 and 3.

The bottom portion (zone A) of the site is in a perfect partial spherical shape. In some case, the zone B is only partially reamed. The dash line 88 has shown where an imaginary hemisphere profile should be. The cylinder portion of the cutting track 95 has a function of direction guidance when the surgeon reinserts the reamer into the site in the correct orientation.

In a robotic operation, the condition check and depth control can be complied by a monitor camera or pre-programmable control. It will avoid the inconvenient step of taking the reamer out from the incision during the operation.

Step 5, alternately reaming the site and adjusting the position of the reamer from the first position 92 to the second position 90 until the reamer forms the second shape (a full continuous hemispherical cutting surface), here called a second cutting component. For the case of a robotic operation, both steps could be either simultaneously or alternately carried out by controlling a stepping motor, so that progressive reaming will be smoother and precise.

Step 6, continues reaming the site while the reamer is in the second position 90 until making sure that the site forms a full continuous hemispherical surface (with a desired dimension, no gap between two zones, see profile 97 in FIG. 2). This step takes less numerous amounts of rotations.

Step 7, removing the reamer from the site, while the reamer is in the second position 90.

A Third Preferred Embodiment of Apparatus

Figure 5A:
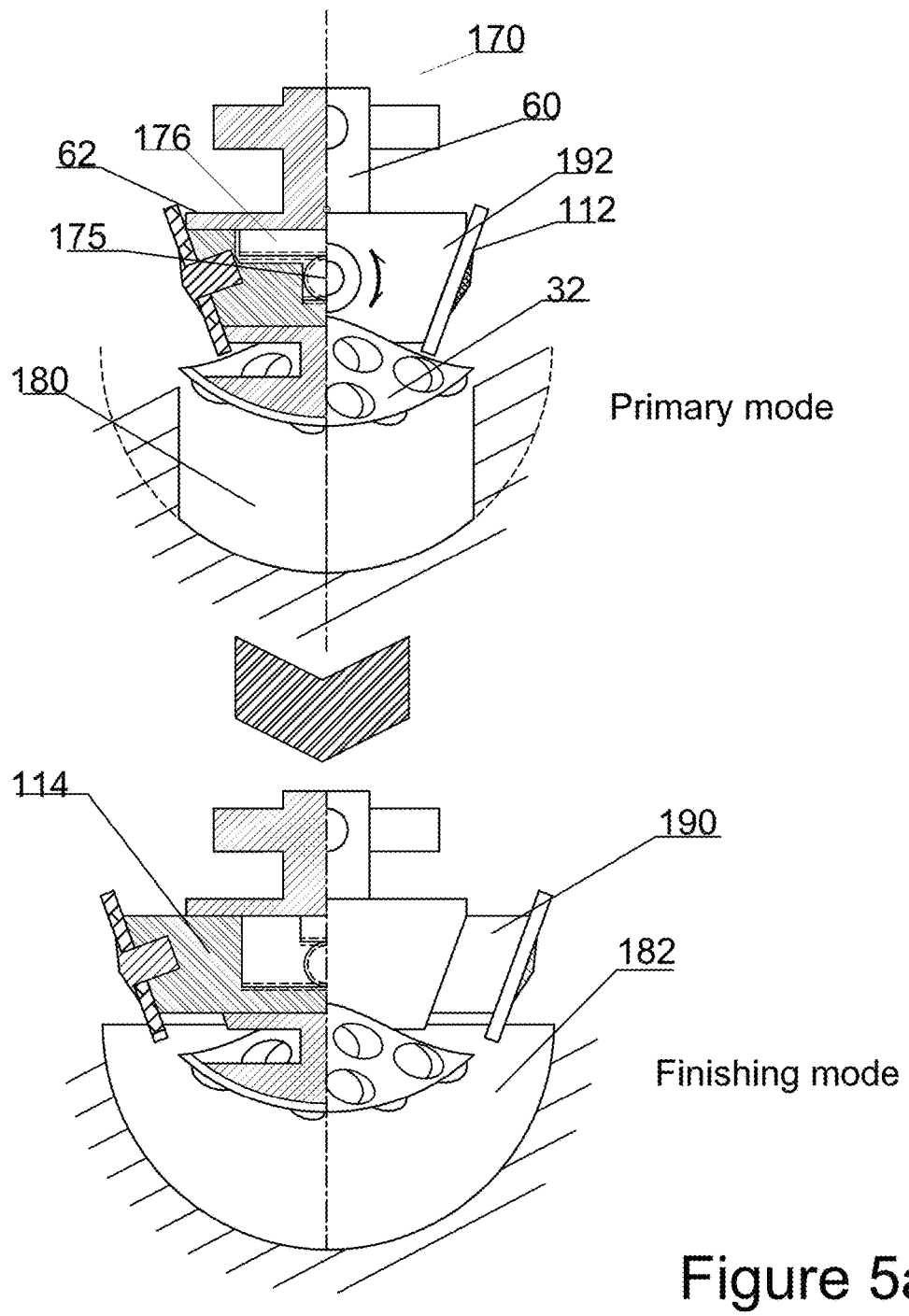
FIG. 5a. An alternative structure of an adjustable reamer has a retractable upper cutting surface configured by offset circular blade as a cutting element.

Instead of spacing away or merging together two cutting surfaces along the longitudinal axis (shift up or down), a structure of the adjustable reamer 10 is able to perform the primary mode in a manner without reaming the upper portion of the hemisphere shown in FIG. 5a. Another type of actuating structure for changing a position/shape of the upper cutting surface 34 could be used to implement the idea of no cutting of the upper section of the hemisphere in the primary cutting mode. For instance, the upper cutting surface 34 could be temporarily "hidden" or retracted within a "collapsed" position, which is nonfunctional and has a much smaller cutting profile during the primary cutting mode. During the finishing mode, one progressively expands the reamer (cutting element(s)) to a second position having the second shape of the reamer (upper cutting surface 34 in functioning), so that the reamer has a full dimension of the hemispherical cutting surface.

According to this principle, both types of blades disclosed both in US 20100076442 and in U.S. Pat. No. 5,755,719 could be conveniently used to configure an upper cutting surface 34 that can be interchangeable between two positions. As the third preferred embodiment of the apparatus shown in FIG. 5a, regardless of the detail of the lower cutting surface 32, a reamer 170 comprises two blades (a preferred one is as disclosed in US 20100076442) for forming the upper cutting surface 34. Each blade is 112 pivotally mounted on the distal end of a slidable/movable arm 114. Each arm is slidable/movable within the tunnel of the two horizontal ends 62 of the second base 60 along horizontal direction. So two blades can be retracted or expanded either outwardly or inwardly by either an actuation mechanism of the driving shaft assembly or manually (a preferred mechanism is a gear 175 and rack 176 combination). A detail of the dimension of each blade and how to properly position of each blade has been disclosed in the US 20100076442 and beyond the coverage of the present invention. Such movements of the blades are corresponding to the first position (retracted) 192 and second (expanded) position 190 of the reamer 170, respectively. But, the entire cutting surface (a cross section), while the reamer in the retracted position, could be much smaller than the one in the second position 90 described as the first embodiment, which makes things easier during the steps of inserting the reamer 170 into the incision. The reamers can partially or not ream the upper section of the hemisphere while it implements the primary mode. The actuating mechanism for adjusting the positions of the reamer could typically use a gear-rack as driving linkage.

A Fourth Preferred Embodiment of Apparatus

An alternative of the third embodiment of apparatus can also be retracted in another kind of "collapsed" format. A pair of swingable circular blades configures the second cutting surface, which swings around the spherical center of the driving shaft. At its lower position, the pair of circular blades has formed a cutting surface which overlaps with the fixed (non-adjustable), lower cutting surface formed by another set of cutting elements (such as a semi-circular blade as disclosed in U.S. Pat. No. 5,755,719 by Frieze). The fixed circular blade here could also be replaced by other kinds of cutting elements discussed above.

Figure 5B:
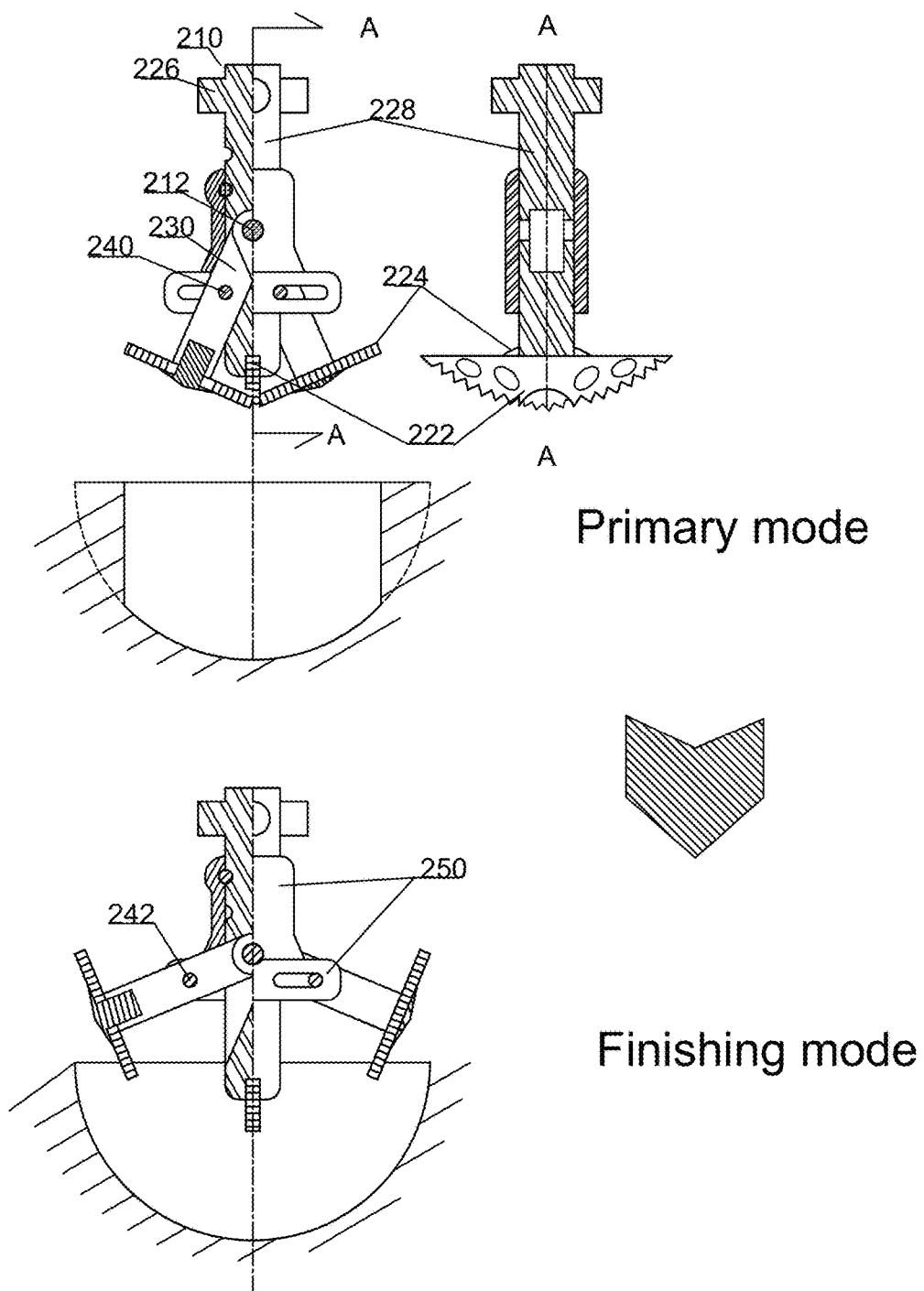
FIG. 5b. An alternative structure of an adjustable reamer has a swingable upper cutting surface configured by offset circular blade as a cutting element.

The fourth embodiment of the apparatus as shown in FIG. 5b, the reamer 210 has been equipped with an upper pair of two circular blades 224 like the one as disclosed in US 20100076442. A frame 228 has an upper end and a bottom end for firmly attaching to a lower cutting surface 32, configured by arch-like cutting element 222 following a principle as disclosed in U.S. Pat. No. 5,755,719 by Frieze, the lower cutting surface covers the area of Zone A. As shown in FIG. 5b. there is an interface 226 at the upper end of the frame 228 for coupling with the driving shaft. A pair of swingable arms 230 is pivotally mounted on a pivot point (spherical center) of the middle section of the frame by its proximal end. The pivot point is equivalent to the virtual spherical center 212 of the cutting surfaces and equivalent to the spherical center of the hemisphere to be cut. Each blade of the upper pair 224 has been pivotally mounted on a distal end of the swingable arm 230, so that the upper pair 224 of the blade has an arrangement in the orthogonal direction (of 90 degree angle) in respect to one of the lower arch-like cutting elements 222. The upper pair 224 of the blade is swingable around the virtual center 212 to a first (retracted) position 240 and to a second (expanded) position 242, respectively. A manual mechanism 250 of locking position affiliated with the frame 228 can be used to adjust the arms 230 to the first position 240 and to the second position 242. When the pair of arms 230 are in the first position 240 (swings to its lower end), the upper pair 224 of circular blade and the lower arch-like cutting elements 222 together form a lower cutting surface 32 of the reamer 210, which presents a dynamic hemispherical cutting profile, while the reamer is rotating. In the finishing mode, the pair of arms 230 swings up to the second position 242 (swings to its upper end) and the upper pair 224 of blades configures an upper cutting surface 34 of the reamer 210. In the meanwhile, the reamer 210 has a full continuous cutting surface formed by both the lower arch-like cutting elements 222 and the upper pair 224 of blades and presents a dynamic hemispherical cutting profile, while the reamer 210 is rotating. Once again, the dimension and position off upper pair 224 of the circular blade in the reamer 210 is determined by a principle and a method as disclosed in US 20100076442 and is beyond coverage of the present invention.

A Second Preferred Embodiment of the Method

With regards to the third and fourth embodiments of apparatus, the corresponding embodiment of the method should be altered from the first preferred embodiment of the method. Due to the smaller profile of the reamer in the first (retracted) position 240 of apparatus described in the third and fourth embodiment, the second preferred embodiment of the method is that of step 3) in the first embodiment of the method could be omitted as well as step 2) becomes directly inserting the reamer on a target site while it is in the first position. The detail of the steps is shown as a flow chart in FIG. 6.

A Fifth Embodiment of the Apparatus

The fifth preferred embodiment of apparatus dedicates that a structure of the reamer(s) is able to perform the primary mode without reaming the upper section of the hemisphere in other manner. As a fifth preferred embodiment of apparatus, there are two pieces of reamers, a primary reamer and a finishing reamer used for a corresponding primary cutting mode and finishing cutting mode, respectively. The primary reamer with a desired dimension, as the first cutting component here, has a fixed, partial hemispherical cutting surface, which envelopes area (Zone A) from the pole to the intermediate latitude of hemisphere as defined above, and is driven by the driving shaft and is able to exclusively ream the lower/bottom portion of the hemisphere. The primary reamer further has a frame with a function for integrally attaching to the cutting surface, such as a thin shell, partial hemispherical dome or others, and directly coupling with the driving shaft for rotation by the interface on its proximal end of the frame. A finishing reamer with a desired dimension, as the second cutting component, has a full continuous hemispherical cutting surface. A typical version is similar to the conventional dome reamer or cutting surface shown by the dynamical hemispherical cutting profile. An important point is that the cutting surfaces of both reamers should have the same spherical cutting radius. The cutting surface here could be configured by any other types of cutting elements and setups, which can generate a hemisphere as discussed above and disclosed in U.S. Pat. No. 5,755,719 by Frieze, in publication of US 20100076442 by Xie and others in the prior art.

A Third Preferred Embodiment of the Method

A third preferred embodiment of the method for reaming the hemispherical surface with a desired dimension corresponding to the apparatus described in the fifth embodiment above comprises the steps shown as a flow chart in FIG. 7 of:

Step A: reaming a bottom (first) portion of a target site by frequently rotating a primary reamer (as the first cutting component) having a first shape around a hemispherical axis, until reaching a desired partial spherical surface, floor condition, and proper depth of the site.

Step B: reaming an entire surface (second portion) of the target site by rotating a fishing reamer (as the second cutting component) having the second shape after step A along same direction as step A until forming a fully continuous hemispherical surface. This step takes fewer rotations compared to step A.

A Sixth Preferred Embodiment of Apparatus

Figure 8:
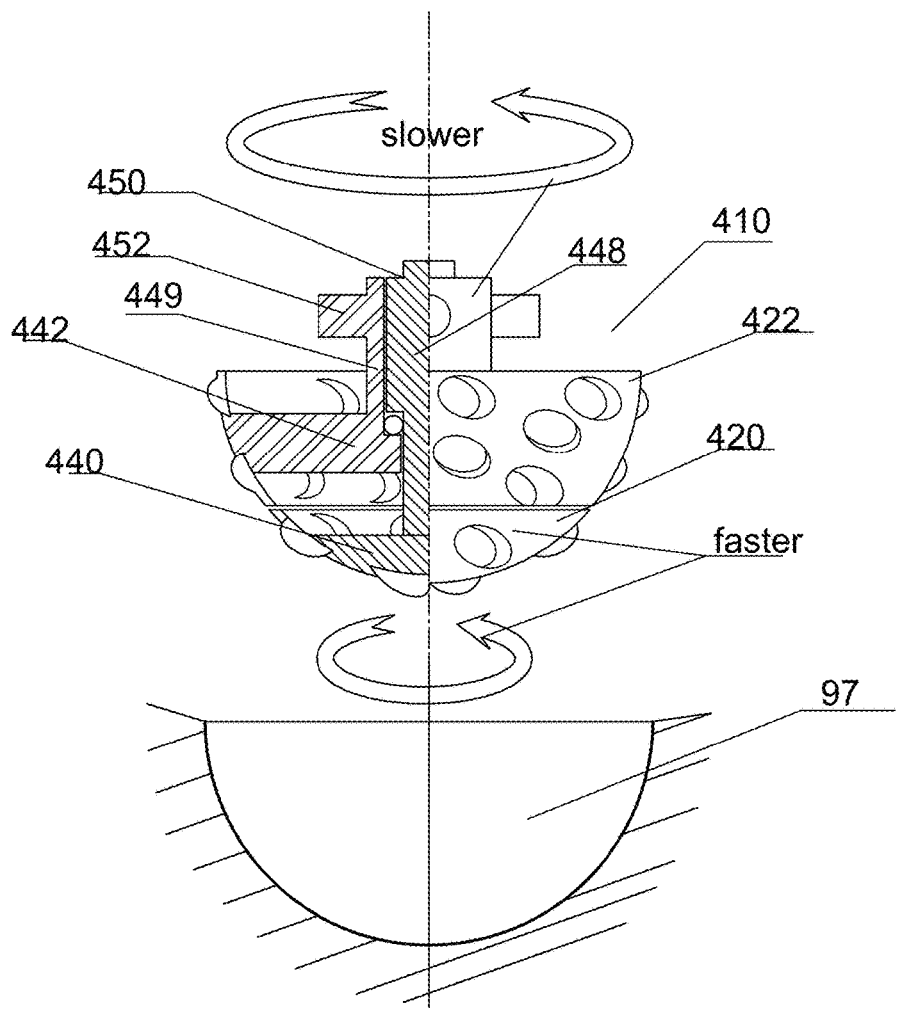
FIG. 8. A structure of a reamer with a lower and an upper cutting surface configured by a cutting element of thin-wall dome, which are able to simultaneously rotate in different speeds along the longitudinal axis of the hemisphere.

As extending the idea of CFC and opposite from the structure of adjustable reamers disclosed above, the sixth embodiment is related to the apparatus, which implements CFC in a manner of applying various cutting frequencies (speed) applied to different regions of the hemisphere. A reamer 410 comprises two layers of the cutting surfaces, a lower and upper cutting surface, arranged in sequence along the longitudinal axis end to end, respectively. As shown in FIG. 8, the cutting element used here is typically of a truncated, hollow thin shell dome, but in a partial hemispherical form with the same spherical cutting diameter. As discussed above, the lower 420 and upper cutting surface 422 correspondingly ream zone A and zone B of the hemisphere, respectively. The two layers of the cutting surface are adjacent, end to end, and form a full hemispherical cutting surface. A first base 440 with a T-shape integrally attached with internal surface of the lower cutting surface by its bottom. A first vertical rod 448 has a first interface 450 at its proximate end for engaging with a first, rod-like driving shaft. A second base 442 with T-shape integrally attached with internal surface of the upper cutting surface 422 by its two horizontal ends and has a second vertical arm 449. The second vertical arm 449 has a staged through-hole at its center along the longitudinal axis and a second interface 452 at its proximal end for engaging with a second, tube-like driving shaft. The through-hole of the second vertical arm 449 has a diameter slidable fit with the first vertical rod 448. The first vertical rod 448 downwardly passes through the through-hole of the second vertical arm 449, pivotally engages with the second base 442 and connects with the first base 440 by its lower end. Each layer of the cutting surface can couple with a corresponding driving shaft of a shaft assembly and rotate independently in terms of direction and speed of rotation. For example, the second interface 452 corresponding to the upper layer of the cutting surface is coupled with and driven by the tube-like shaft at a relative lower rotating speed and the first interface 450 corresponding to the lower layer of the cutting surface is simultaneously coupled with and driven by the rod-like shaft at a relative higher rotating speed, respectively. The difference of turning speed (frequency) between two cutting layers is at least 2 folds. In general, the cutting surface configured by any type of cutting element is also appropriate for this CFC design.

A Fourth Preferred Embodiment of the Method

A fourth method for preparing a fully continuous hemispherical surface with a desired dimension comprising steps of:

reaming a lower portion of a target site by rotating a first cutting surface of a reamer around a longitudinal axis of a hemisphere at a higher rotating frequency in order that the site has a desired depth and is at least in a partial hemispherical form defined from pole to an intermediate latitude of the hemisphere; and simultaneously reaming an upper portion of the site by rotating a second cutting surface of the reamer around the longitudinal axis at a lower rotating frequency until the site is in a continuous hemisphere form, wherein the first and second cutting surface have an identical spherical cutting radius and rotate independently in terms of a rotating direction and a rotating frequency there of, wherein the intermediate latitude locates between the pole and the equator of the hemisphere and has a latitudinal range defined from 35 to 55 degrees while the latitude of the pole is 90 degrees. The step of reaming the lower portion is implemented in at least two folds frequency of rotation than the step of reaming the upper portion implemented.

In Summary, the Methods of CFC could be implemented in two fashions:

First one: a primary step is cutting the bottom portion of the target site in multiple number times of rotation and postpone cutting the upper portion of the site by either retracting the upper cutting surface or shifting the upper cutting surface of the adjustable reamer (in first position) away from spherical center or by a primary reamer. A secondary step is using a reamer having fully hemispherical cutting surface to ream the entire site to form a full continuous hemispherical surface. The fully hemispherical cutting surface here could be an individual reamer (a finishing reamer) or an adjustable reamer with both lower and upper cutting surface that are in a fully functional position.

Second one: a reamer has both lower and upper cutting surfaces arranged in end to end fashion to form a continuous hemispherical cutting surface. The two cutting surfaces adjacent to each other simultaneously ream the corresponding portion of the site, but are driven by separated shafts in different cutting speeds or directions. The lower one runs in higher rotational speed (frequency) than the upper one in order to compensate the radius difference between the regions.

Multiple variations and modifications are possible in the embodiments of the invention described here, such as any types of cutting elements are applicable to configure a cutting surface of the reamer and any alternative ways to assemble a reamer, which is suitable for the methods of reaming the hemispherical surface in various steps discussed in the present invention. Although certain illustrative embodiments of the invention have been shown and described here, a wide range of modifications, changes, and substitutions is contemplated in the foregoing disclosure. While the above description contains many specifics, these should not be seen as limitations on the scope of the invention, but rather as exemplifications of one or the other preferred embodiment thereof. In some instances, some features of the present invention may be employed without a corresponding use of the other features. Accordingly, it is appropriate that the foregoing description be construed broadly and understood as being given, by way of illustration and example only, the spirit and scope of the invention being limited only by the appended claims.

What we claim:

1. A composite reamer being attachable to a driving shaft and rotatable around a longitudinal axis of the shaft for preparing a desired hemispheric surface having a first radius, a spherical center, a pole, an equator and a rotational axis, respectively, comprising:
   a lower cutting element configured to couple to a lower frame to form a lower cutting portion of the reamer with a lower cutting surface for reaming a first portion defined from the pole to an intermediate latitude of the desired hemispheric surface, the lower cutting surface having a lower spherical cutting center and a lower rotational axis; and
   an upper cutting element configured to couple to an upper frame to form an upper cutting portion of the reamer with an upper cutting surface for reaming at least a second portion defined from the intermediate latitude to the equator of the desired hemispheric surface, the upper cutting surface having an upper spherical cutting center and an upper rotational axis;
   wherein the lower and upper rotational axis are coaxial with the longitudinal axis of the shaft, when the reamer is in the primary mode, the upper cutting elements depart from the second portion so that the first portion of the desired hemispherical surface is reamed, and in the finishing mode, the upper and lower cutting elements are connected end-to-end to form a continuous hemispheric cutting surface for reaming the first and second portion of the desired hemispherical surface.

2. The composite reamer of claim 1, wherein the upper and lower cutting surfaces define a hemispherical surface having a second radius identical to the first radius of the desired hemispheric surface to be cut.

3. The composite reamer of claim 2, wherein each of the lower and the upper cutting surfaces is a partial dome.

4. The composite reamer of claim 2, wherein the upper frame further comprises an upper interface configured to couple the driving shaft, so that the upper frame forms a fixed part of the composite reamer, and the lower frame forms a moveable part of the composite reamer.

5. The composite reamer of claim 2, wherein, the lower frame further comprises an upper interface configured to couple to the driving shaft, so that the lower frame forms a fixed part of the reamer, and the lower frame comprises a lower interface configured to couple to the upper frame so that the upper frame forms a moveable part of the composite reamer.

6. A method for preparing a desired hemispheric surface having a first radius, a spherical center, a pole, an equator and a rotational axis, respectively, comprising the steps of:
   setting a composite reamer of claim 2 in a primary cutting mode, while the lower cutting element is able to ream a first portion defined from pole to an intermediate latitude of the desired hemispheric surface and the upper cutting elements depart from a second portion defined from the intermediate latitude to the equator of the desired hemispheric surface;
   inserting the composite reamer of claim 2 into a target site of the desired hemispheric surface;
   aligning the composite reamer coaxially with a longitudinal axis of the shaft the pole of the desired hemispheric surface;
   reaming the first portion of the desired hemispheric surface by rotating the composite reamer for a first cutting time period;
   setting the composite reamer in a finishing cutting mode, the upper and lower cutting elements are end-to-end connected to form a continuous hemispherical cutting surface;
   reaming both the first portion and the second portion of the desired hemispheric surface by rotating the composite reamer for a second cutting time period.

7. The method of claim 6, wherein the step of reaming the first and second portion is performed without removing the reamer from the target area.

8. The method of claim 6, wherein the intermediate latitude is at a location between 35 to 55 degrees from the pole to the equator of the hemispheric surface, while the equator and the pole is at 0 and 90 degrees latitude, respectively.

9. The method of claim 6, wherein the intermediate latitude is at 45 degrees latitude of the hemispheric surface.

10. The method of claim 6, wherein the first cutting time period of the primary cutting mode lasts at least twice as long as the second cutting time period of the finishing cutting mode.

11. The method of claim 6, wherein each of the lower and upper cutting elements has at least one cutting surface and is able to generate at least a partial hemispheric surface; while rotating around the longitudinal axis of the shaft.

12. The method of claim 6, wherein the hemispherical cutting surface has either convex or concave portions.

* * * * *